US011832941B2

(12) United States Patent
Zhang et al.

(10) Patent No.: US 11,832,941 B2
(45) Date of Patent: Dec. 5, 2023

(54) METHOD FOR FABRICATING WEARABLE HYDROGEL GLUCOSE SENSOR

(71) Applicant: JOINT SHANTOU INTERNATIONAL EYE CENTER OF SHANTOU UNIVERSITY AND THE CHINESE UNIVERSITY OF HONG KONG, Shantou (CN)

(72) Inventors: Mingzhi Zhang, Shantou (CN); Hang Qu, Shantou (CN); Xuehao Hu, Shantou (CN); Xin Wen, Shantou (CN); Qingping Liu, Shantou (CN)

(73) Assignee: JOINT SHANTOU INTERNATIONAL EYE CENTER OF SHANTOU UNIVERSITY AND THE CHINESE UNIVERSITY OF HONG KONG, Shantou (CN)

( * ) Notice: Subject to any disclaimer, the term of this patent is extended or adjusted under 35 U.S.C. 154(b) by 0 days.

(21) Appl. No.: 18/066,517

(22) Filed: Dec. 15, 2022

(65) Prior Publication Data

US 2023/0200686 A1    Jun. 29, 2023

(30) Foreign Application Priority Data

Dec. 24, 2021    (CN) .......................... 202111596645.2

(51) Int. Cl.
*A61B 5/145*   (2006.01)
*C08J 5/18*    (2006.01)
*C08J 3/075*   (2006.01)

(52) U.S. Cl.
CPC ........... *A61B 5/14532* (2013.01); *C08J 3/075* (2013.01); *C08J 5/18* (2013.01); *A61B 2562/12* (2013.01); *C08J 2333/26* (2013.01)

(58) Field of Classification Search
None
See application file for complete search history.

(56) References Cited

U.S. PATENT DOCUMENTS 6,485,703 B1 *   11/2002   Cote .................... G01N 33/66
                                                            424/9.1
2015/0087945 A1 *   3/2015   Ziaie .................... A61B 5/0031
                                                            29/846

FOREIGN PATENT DOCUMENTS

CN         102727218 A        10/2012
CN         105499806 A        4/2016
(Continued)

OTHER PUBLICATIONS

CN108107021_translation (Year: 2018).*
(Continued)

*Primary Examiner* — Manuel A Mendez
(74) *Attorney, Agent, or Firm* — Stuart H. Mayer; Kaplan Breyer Schwarz, LLP

(57) ABSTRACT

Disclosed is a method for fabricating a wearable hydrogel glucose sensor, belonging to the technical field of biomedical sensing, including using polyacrylamide hydrogel as a basic material, preparing a hydrogel film by adding with phenylboronic acid group capable of recognizing glucose molecules, and carrying out grating writing on the hydrogel film in a femtosecond laser direct writing mode to obtain the wearable hydrogel glucose sensor. The hydrogel film combines with glucose and expands linearly, which makes the grating period and effective refractive index change. The quantitative measurement of glucose is realized by detecting the spatial position of diffraction band and the change of diffraction power intensity.

2 Claims, 7 Drawing Sheets

(56) References Cited

FOREIGN PATENT DOCUMENTS

| | | |
|---|---|---|
| CN | 108051377 A | 5/2018 |
| CN | 108107021 A | 6/2018 |
| CN | 110527023 A | 12/2019 |
| IN | 113171091 A | 7/2021 |
| WO | 2015053975 A1 | 4/2015 |
| WO | WO-2015053975 A1 * | 4/2015 ......... A61B 5/14532 |

OTHER PUBLICATIONS

CN110527023_translation (Year: 2019).*
CN113171091_translation (Year: 2021).*
CN102727218_translation (Year: 2011).*
CN105499806_translation (Year: 2016).*
CN108051377_translation (Year: 2017).*
Liu et al. "Direct light written holographic volume grating as a novel optical platform for sensing characterization of solution" Optics and Laser Technology 109 (2019) 510-517.
Chen et al. "Synthesis and properties of fast-response glucose-sensitive hydrogels containing immobilized phenylboronic acid" Oct. 2016, vol. 46, No. 5 Journal of Northwest University.

* cited by examiner

METHOD FOR FABRICATING WEARABLE HYDROGEL GLUCOSE SENSOR

CROSS-REFERENCE TO RELATED APPLICATIONS

This application claims priority to Chinese Patent Application No. 202111596645.2, filed on Dec. 24, 2021, the contents of which are hereby incorporated by reference.

TECHNICAL FIELD

The present application relates to the technical field of biomedical sensing, and in particular to a method for fabricating a wearable hydrogel glucose sensor.

BACKGROUND

Diabetes is a vascular disease with a high prevalence in the world, the hazard of which lies in serious complications; for diabetic patients, it is particularly important to monitor their blood glucose, which currently involves two available methods; one is to measure glucose concentration by a glucometer, requiring pricking the skin of the finger and taking peripheral blood for examination; although relatively simple, this method is invasive, discontinuous, and requires operation of high frequency, causing physiological pain to the patient, and the discrete data are not conducive to the physician's judgment of the condition and adjustment of the protocol. The other method involves a continuous glucose monitoring system, which overcomes the disadvantage of not being able to measure continuously, but it is also invasive and requires periodic calibration and replacement. Therefore, it is necessary to develop a blood glucose monitoring device for non-invasive and continuous blood glucose monitoring.

SUMMARY

The present application provides a method for fabricating a wearable hydrogel glucose sensor in order to overcome the above-mentioned drawbacks, including fabricating a grating-based glucose sensor with grating inscription based on a femtosecond laser. The method is highly sensitive, stable and responsive.

To achieve the above objectives, the present application provides the following technical schemes:

a method for fabricating a wearable hydrogel glucose sensor, including using polyacrylamide hydrogel as a basic material, fabricating a hydrogel film by adding with phenylboronic acid group capable of recognizing glucose molecules, and carrying out grating writing on the hydrogel film in a femtosecond laser direct writing mode to obtain the wearable hydrogel glucose sensor (i.e., grating sensor).

The prepared polyacrylamide hydrogel is stored in phosphate buffer solution (PBS) under darkness for later use.

Optionally, the hydrogel film is prepared as follows: mixing 30 percent (%) acrylamide solution, sodium dodecyl sulfate, ammonium persulfate, N,N,N',N'-methyl ethylenediamine, and 3-acrylamide phenylboronic acid solution to obtain a prepolymer solution, quickly sucking 60-100 microliters (μL) and dropping onto a glass slide, with a cover glass above so as to make the hydrogel film a uniform thickness; adjusting the thickness of the hydrogel film by adding spacers on both sides of the glass slide and standing at room temperature for 1-2 hours (h) to obtain a transparent hydrogel film.

Optionally, the grating writing is carried out as follows: placing the hydrogel film on a three-axis displacement table of a femtosecond laser, performing grating writing with visible light of 520 nanometers (nm), observing a writing process in real time with a camera system (40 times objective lens), with a distance of laser lens from the hydrogel film being 3-5 micrometers (um).

Optionally, the grating writing is performed in a writing speed of 50-100 micrometers/second (um/s), with a writing power of 0.282-0.564 microjoule (uJ).

The present application also provides a wearable hydrogel glucose sensor obtained according to the method for fabricating a wearable hydrogel glucose sensor.

The present application also provides an application of the wearable hydrogel glucose sensor in fabricating products for monitoring glucose level.

Principle of quantitative determination of glucose in tears: the hydrogel film binds to glucose and exhibits linear expansion, causing changes in grating period and effective refractive index; and a quantitative measurement of glucose is achieved by detecting a spatial position of diffracted spectral bands and changes in diffracted power intensity.

Compared with the prior art, the present application has the advantages that:

firstly, the present application provides a simple preparation process, with polymerization occurs at room temperature without additional equipment, and prepared polyacrylamide hydrogel is more practical with improved transparency as comparing to that prepared by existing technology;

secondly, the wearable hydrogel glucose sensor prepared by the present application is placed on the eye, and the transparent hydrogel film can non-invasively monitor the glucose concentration in the tear fluid without affecting the patient's vision, thus effectively reflecting the glucose level of the body; and thirdly, the grating writing of the femtosecond laser used in the present application is more flexible, and the parameters can be adjusted in real time according to different materials and states, enabling a wide range of applications.

BRIEF DESCRIPTION OF THE DRAWINGS

In order to more clearly explain the embodiments of the present application or the technical schemes in the prior art, the following will briefly introduce the drawings to be used in the embodiments. Obviously, the drawings in the following description are only some embodiments of the present invention. For those of ordinary skill in the art, other drawings may be obtained according to these drawings without any creative efforts.

DETAILED DESCRIPTION OF THE EMBODIMENTS

Figure 1:
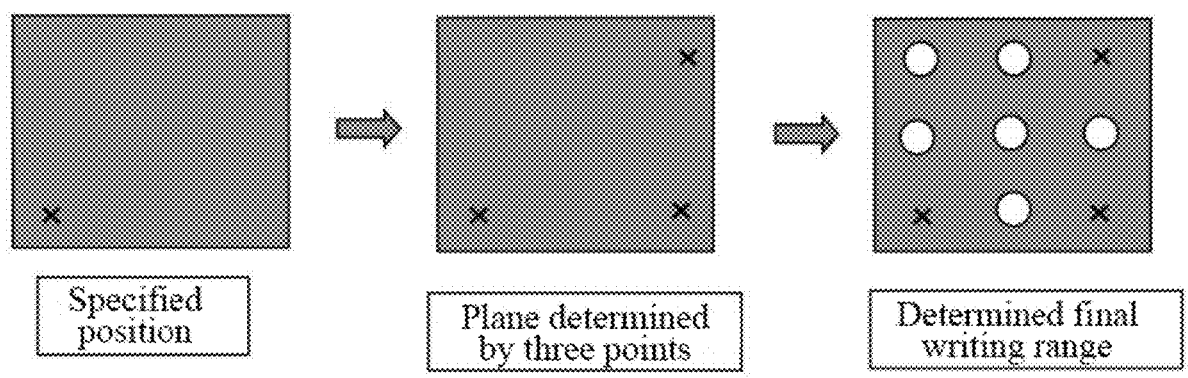
FIG. 1 illustrates a processing of determining a writing range on hydrogel film.

Now various exemplary embodiments of the present application will be described in detail. This detailed description should not be taken as a limitation of the present application, but should be understood as a rather detailed description of some aspects, characteristics and embodiments of the present application.

It should be understood that the terms mentioned in the present invention are only used to describe specific embodiments, and are not used to limit the present application. In addition, for the numerical range in the present application, it should be understood that each intermediate value between the upper limit and the lower limit of the range is also specifically disclosed. Every smaller range between any stated value or the intermediate value within the stated range and any other stated value or the intermediate value within the stated range is also included in the present application. The upper and lower limits of these smaller ranges can be independently included or excluded from the range.

Unless otherwise stated, all technical and scientific terms used herein have the same meanings commonly understood by those of ordinary skill in the field to which this application relates. Although the present application only describes preferred methods and materials, any methods and materials similar or equivalent to those described herein can be used in the practice or testing of the present application. All documents mentioned in this specification are incorporated by reference to disclose and describe the methods and/or materials related to the documents. In case of conflict with any incorporated documents, the contents of this specification shall prevail.

Without departing from the scope or spirit of the present application, it is obvious to those skilled in the art that many modifications and changes can be made to the specific embodiments of the present specification. Other embodiments obtained from the description of the present application will be obvious to the skilled person. The specification and embodiment of this application are only exemplary.

As used in this paper, the terms "comprising", "including", "having" and "containing" are all open terms, meaning including but not limited to.

The embodiments of the present application use a femtosecond laser of SpOne-8-SHG, produced by Newport, America.

Embodiments 1-5

30 percent (%) (weight/volume, w/v) acrylamide solution, 10 weight percentage (wt %) sodium dodecyl sulfate (SDS), 10 wt % ammonium persulfate (AP), 10 wt % N,N,N',N'-Tetramethylethylenediamine (TEMED) and 20 mole percent (mol %) 3-acrylamidophenylboronic acid (3-APBA) solution are mixed to prepare a prepolymer solution, then 80 microliters (uL) of which is quickly sucked and dropped onto a glass slide, with a cover glass above so as to make the hydrogel film a uniform thickness, followed by standing at room temperature for 1.5 hours (h) to obtain a transparent hydrogel film.

The hydrogel film is placed on a three-axis displacement table of a femtosecond laser, and subjected to grating writing with visible light of 520 nanometers (nm), where a writing process is observed by a camera system, with a distance of laser lens from the hydrogel film being 4 micrometers (um), a writing speed of 100 micrometers/second (um/s), a writing power of microjoule (uJ), then a wearable hydrogel glucose sensor (i.e. grating sensor) is obtained.

With different amounts of raw materials as shown in Table 1, polyacrylamide hydrogels with concentrations of 6%, 8%, 10%, 12.5% and 15% are prepared respectively, where the 5 embodiments all adopt a 1,000 uL system, where the 30% (w/v) acrylamide added are of different amounts and polyacrylamide hydrogels with different concentrations are therefore prepared.

TABLE 1

|  | Embodiment 1 | Embodiment 2 | Embodiment 3 | Embodiment 4 | Embodiment 5 |
| --- | --- | --- | --- | --- | --- |
| 20 moL % 3-APBA solution (μL) | 780 | 720 | 640 | 560 | 480 |
| 30% (w/v) Acrylamide solution (μL) | 200 | 260 | 340 | 420 | 500 |
| 10 wt % SDS (μL) | 10 | 10 | 10 | 10 | 10 |
| 10 wt % AP (μL) | 10 | 10 | 10 | 10 | 10 |
| 10 wt % TEMED (μL) | 0.8 | 0.6 | 0.4 | 0.4 | 0.4 |

FIG. 1 shows a processing of determining a writing range on hydrogel film. It can be seen from the figure that a certain position is specified first, then a plane is determined by three points, and then the final writing range is determined.

Figure 2:
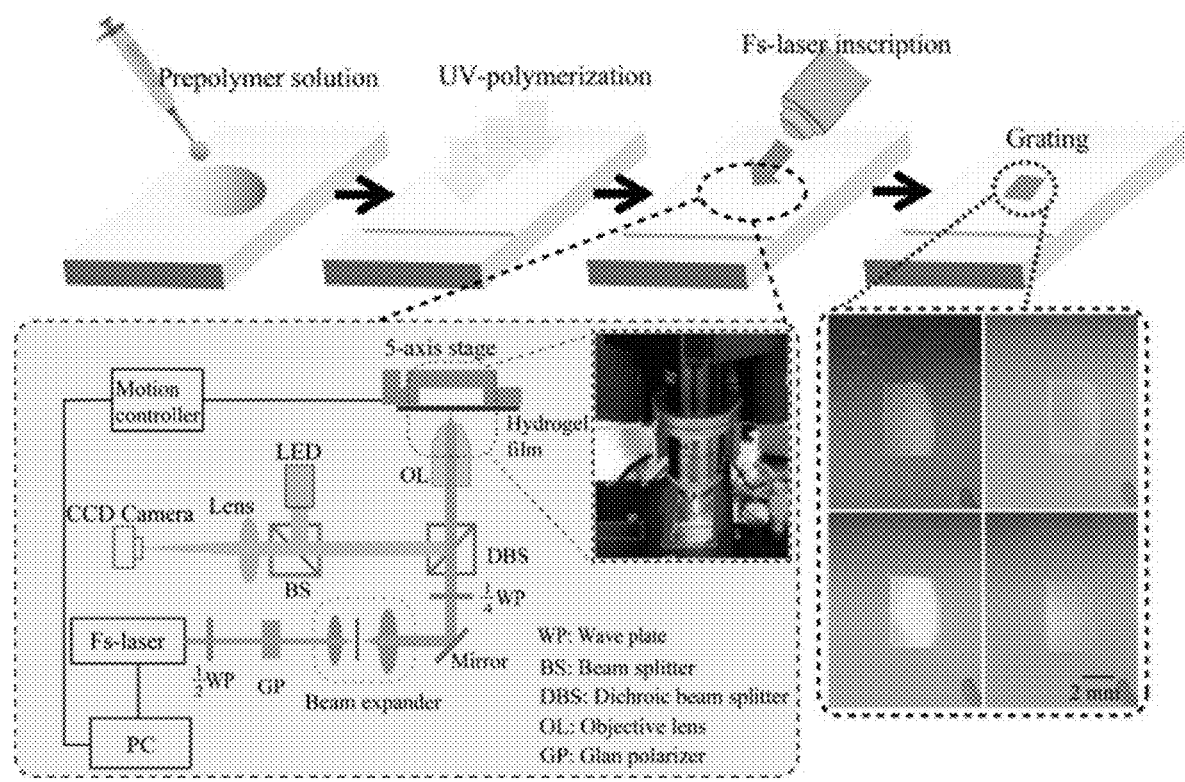
FIG. 2 shows a fabricating process of a grating sensor.

FIG. 2 shows a fabricating process of a grating sensor.

Figure 3:
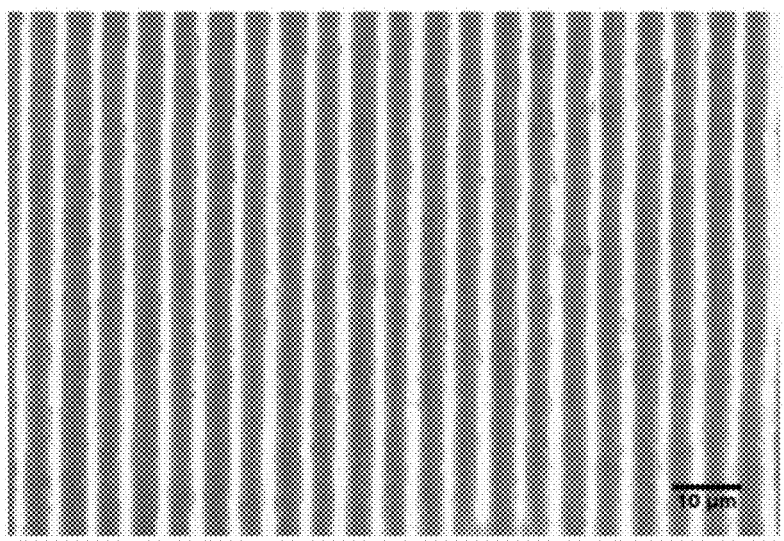
FIG. 3 shows an image of a grating under a microscope of a camera system.

FIG. 3 shows an image of a grating in Embodiment 1 under a 40× microscope of the camera system, and it can be seen from the figure that the grating has a period of 5 um, uniform shape and neat arrangement, which indicates that the writing is successful.

Different concentrations of glucose solutions are prepared and a linear correlation curve is plotted, with specific process as follows:

(1) fabricating glucose solutions of 0 millimolar (mM), 10 mM, 20 mM, 30 mM, 40 mM and 50 mM respectively;
(2) placing the film in PBS solution for 2 h to make it stable;
(3) respectively placing the film in the glucose solutions for 1 h according to the concentration gradient, and measuring the thickness of the film in each concentration gradient; and
(4) establishing a linear correlation between glucose concentrations and film thickness.

Figure 4:
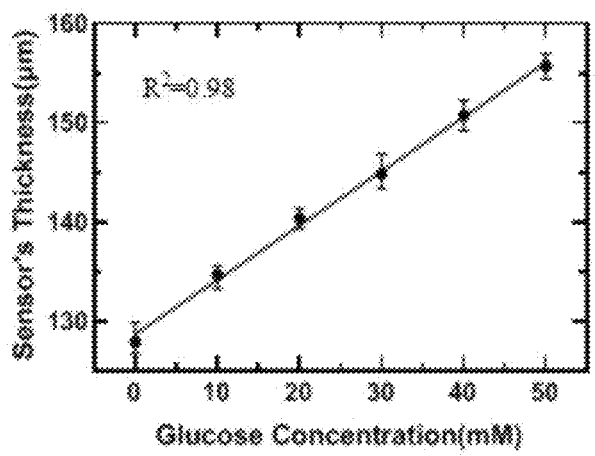
FIG. 4 shows a linear plot of cross-sectional thickness of the grating sensor at different glucose concentrations.

As shown in FIG. 4, it can be seen that the film thickness has a good linear correlation with glucose solutions of 0-50 mM, indicating that the film has good swelling property when combined with glucose.

Figure 5:
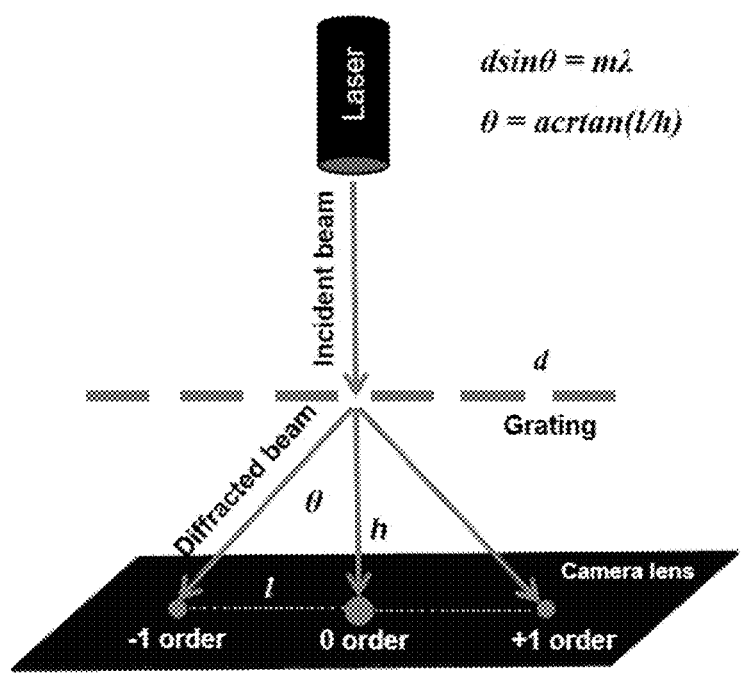
FIG. 5 shows a schematic diagram of a grating irradiated by a 632 nanometers (nm) Heliun-Neon (He—Ne) laser.

FIG. 5 shows a schematic diagram of a grating irradiated by He—Ne laser, and it can be seen from the figure that a linear relationship between glucose concentration and spatial position of spectral band is established according to the principle of grating diffraction, then, the diffraction power intensity changed, and the glucose concentration can be quantitatively detected.

Figure 6:
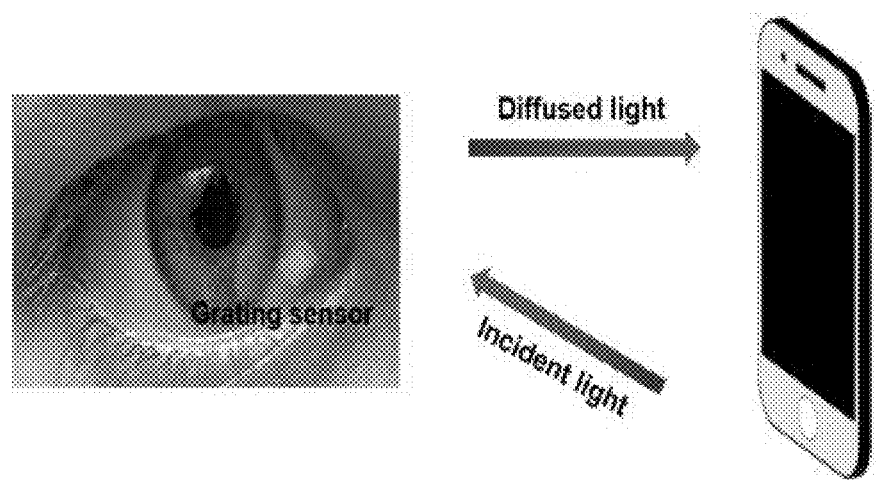
FIG. 6 illustrates an operation of the grating sensor for smartphone detection.
Figure 7:
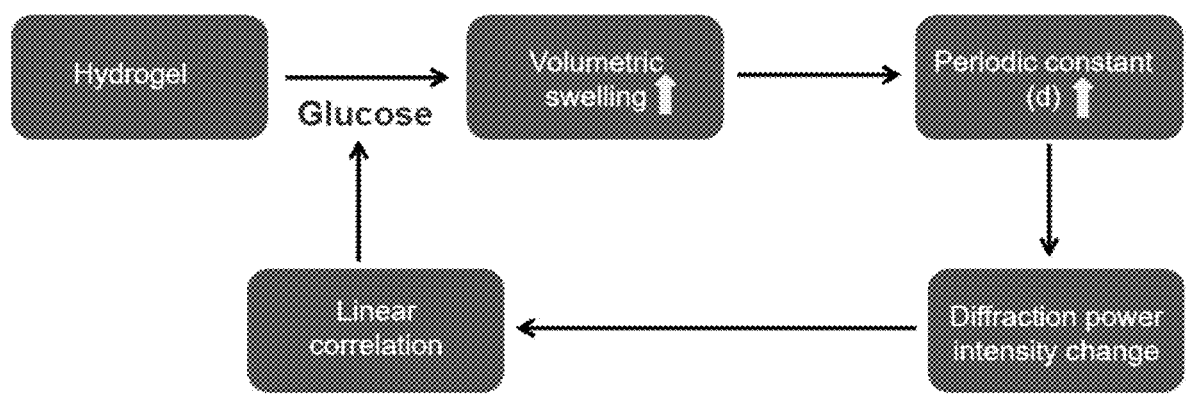
FIG. 7 is a diagram illustrating a principle of glucose quantification in tears.

Specific Application:

The grating sensor prepared in Embodiment 1 is placed in the eye, and the grating is irradiated by the incident light from a smartphone to detect the spatial position of the spectral band. By establishing the linear relationship between diffraction power intensity and glucose concentrations, the quantitative detection of glucose in tears is realized. See FIG. 6 and FIG. 7 for details.

Embodiment 6

Same as Embodiment 1, except that a phase mask plate is used to write the grating to obtain the grating sensor.

Embodiment 7

Acrylamide, N,N'-Methylenebisacrylamide and 3-APBA are mixed in a ratio of 78.5 mol %:1.5 mol %:20 mol % to obtain a mixed solution, then 1 mL of dimethyl sulfoxide and the photoinitiator 2,2-Diethoxy Acetophenone (DEAP) (20 uL) or 2,2dimethoxy-2-phenylacetophenone (DMPA) (2% (w/v)) is added, followed by stirring at room temperature and fully dissolving; the above solution is drop added onto the glass slide, and is covered with a cover glass on the top to maintain a uniform thickness, followed by irradiation with ultraviolet light (365 nm) for 10 minutes (min) to obtain a transparent and uniform hydrogel film.

Other operations are the same as in Embodiment 1.

Embodiment 8

Same as Embodiment 1, except that the writing speed of the present embodiment is 100 um/s.

Embodiment 9

Same as in Embodiment 1, except that the writing speed of the present embodiment is 100 um/s.

Test Embodiment

A control group is arranged using the traditional glucometer test method, and the grating sensor prepared in Embodiments 1-3 are used to test the glucose level, and a final average value is obtained after several repeated tests, with results as shown in Table 2.

TABLE 2

|  | Glucose level mmol/L | Accuracy % |
| --- | --- | --- |
| Control group | 9.8 | — |
| Embodiment 1 | 9.35 | 95.4 |

TABLE 2-continued

|  | Glucose level mmol/L | Accuracy % |
| --- | --- | --- |
| Embodiment 2 | 9.02 | 92.0 |
| Embodiment 3 | 8.86 | 90.4 |

Note: accuracy refers to the accuracy of the measured glucose level compared with the control group.

As can be seen from Table 2, compared with that of blood glucose meter (glucometer) test (glucose oxidase method), the accuracy of grating sensor prepared in Embodiment 1 (phenylboronic acid method) is 95.4%, while that of grating sensor prepared in Embodiment 2 is 92.0%, and that of grating sensor prepared in Embodiment 3 is 90.4%.

The above describes only the preferred embodiments of the present application and is not intended to limit the present application. Any modifications, equivalent substitutions and improvements made within the spirit and principles of the present application shall be included in the scope of protection of the present application.

What is claimed is:

1. A method for fabricating a wearable hydrogel glucose sensor, comprising the steps of: using polyacrylamide hydrogel as a basic material, preparing a hydrogel film by adding 3-acrylamide phenylboric acid (3-APBA) with a phenylboronic acid group capable of recognizing glucose molecules, and carrying out grating writing on the hydrogel film in a femtosecond laser direct writing mode to create the wearable hydrogel glucose sensor; wherein:

preparing the hydrogel film comprises the steps of: mixing 30% acrylamide solution, sodium dodecyl sulfate, ammonium persulfate, N,N,N',N'-methyl ethylenediamine, and 3-acrylamide phenylboronic acid solution to obtain a prepolymer solution, quickly sucking 60-100 microliters (uL) of the prepolymer solution and dropping onto a glass slide; adjusting a thickness of the hydrogel film by adding spacers on both sides of the glass slide, covering a transparent hydrogel film above the glass slide, and maintaining at room temperature for 1-2 hours (h) to obtain a transparent hydrogel film; and the grating writing comprising the steps of: placing the hydrogel film on a three-axis displacement table of a femtosecond laser, performing grating writing with visible light of 520 nanometers (nm), observing a writing process in real time with a camera system having a distance of laser lens from the hydrogel film of 3-5 micrometers (um); and the grating writing is performed at a writing speed of 50-100 micrometers/second (um/s), with a writing power of 0.282-0.564 microjoule (uJ).

2. A wearable hydrogel glucose sensor arrangement comprising:

a hydrogel grating sensor fabricated in accordance with the the method of claim 1; and a smartphone for irradiating the hydrogel grating sensor and monitoring glucose concentrations.

* * * * *